United States Patent [19]
Kidd

[11] Patent Number: 5,831,172
[45] Date of Patent: Nov. 3, 1998

[54] VEHICLE SAFETY BELT TEST APPARATUS AND METHOD

[76] Inventor: James Kidd, Box 1057, Barry's Bay, Ontario, Canada, K0J 1B0

[21] Appl. No.: 882,373

[22] Filed: Jun. 25, 1997

[51] Int. Cl.$^6$ ........................................................ G01L 1/00
[52] U.S. Cl. .................. 73/828; 73/862.42; 73/862.451; 73/862.391
[58] Field of Search ........................ 73/826, 828, 862.391, 73/862.42, 862.44, 862.451, 862.454, 862.471

[56] References Cited

U.S. PATENT DOCUMENTS

| | | | |
|---|---|---|---|
| 3,817,093 | 6/1974 | Williams | 73/862.474 |
| 4,932,722 | 6/1990 | Motozawa | 297/480 |
| 5,221,110 | 6/1993 | Hamaue | 297/480 |
| 5,329,822 | 7/1994 | Hartel et al. | 73/862.61 |
| 5,496,068 | 3/1996 | Ball et al. | 280/806 |
| 5,558,370 | 9/1996 | Behr | 280/807 |

*Primary Examiner*—Max H. Noori
*Attorney, Agent, or Firm*—Swabey Ogilvy Renault; Guy J. Houle

[57] ABSTRACT

A vehicle safety belt test apparatus and method is described. The apparatus is comprised of a frame which is adapted to be positioned on a seat of a vehicle and disposed to distribute pressure substantially evenly on the seat. One or more pistons are secured to the frame and to a seat belt support curved member. The support curved member is adapted to receive opposed free ends of two spaced-apart seat belt portions of a seat belt thereover with a buckle of the seat belt securing the opposed free ends together. The seat belt portions are secured at a securing end to a frame of a vehicle. A pressure control device is provided to actuate the pistons to displace the seat belt support member relative to the frame whereby to exert a predetermined force on the seat belt portions to test the restraining strength of the seat belt.

11 Claims, 2 Drawing Sheets

VEHICLE SAFETY BELT TEST APPARATUS AND METHOD

TECHNICAL FIELD

The present invention relates to a vehicle safety belt test apparatus and method.

BACKGROUND ART

Currently vehicle seat belts are verified for mechanical defects by mechanically inclined people, such as mechanics that work in automobile sales and repair establishments. Manual verification of the seat belts is currently made to determine if the belts and their buckles are in good condition and also if there is proper attachment of the seat belt to the floor or side posts or roof structure of the vehicle. These tests are effected manually such as by pulling the shoulder strap portion of the safety harness by giving it a quick pull to ensure that their clutch engages to stop the belt immediately upon being subject to a quick pull action. The belt buckles are also closed and open and fastened together to determine that they work properly. An overall visual check is also made to inspect the belts for worn or frayed areas and to inspect the floor and post structure around the securement fasteners of the belt to make sure that the floor and frame is not damaged by rust. Safety regulations require that each time a vehicle is re-sold to be driven on the road, it has to undergo a safety check by properly licensed mechanics. Because road salt induces metal corrosion and metal fatigue, the above visual test procedure is considered to be inadequate to detect metal defects. There is therefore a need to provide an improved manner of verifying the safety aspect of seat belts.

SUMMARY OF INVENTION

It is a feature of the present invention to provide a vehicle safety belt test apparatus and method which overcomes the above-mentioned disadvantages of the prior art.

Another feature of the present invention is to provide a vehicle safety belt test apparatus and method which is easy to install and operate and which will provide proper testing of the seat belt to assure that it can resist to the desired load stresses that are imparted thereto during a collision of the vehicle.

According to the above features, from a broad aspect, the present invention provides a vehicle safety belt test apparatus which comprises a frame adapted to be positioned on a seat of the vehicle and having interconnected frame members disposed to distribute pressure substantially evenly on the seat. Piston means is secured to the frame. Seat belt support means is secured to the piston means and adapted to receive opposed free ends of two spaced-apart seat belt portions of a seat belt thereover with a buckle of the seat belt securing the opposed free ends together over the belt support means. The seat belt portions are secured at a securing end to a frame of the vehicle. Control means is provided to actuate the piston means to displace the seat belt support means relative to the frame to exert a predetermined force on the seat belt portions to test the restraining strength of the seat belt and its attachments.

According to a further broad aspect of the present invention there is provided a method of testing the strength of a seat belt and comprising the steps of positioning a support frame at a desired location on a vehicle seat. Opposed free ends of two spaced-apart seat belt portions are positioned over a seat belt support means. The seat belt support means is secured to piston means secured to the support frame. Buckle portions which are attached to the seat belt portions are secured together with the belt portions taut over the support means. The piston means is actuated by control means whereby to apply a predetermined force on the seat belt. At least a part of the predetermined force is removed and the seat belt is then inspected as well as its attachments to detect any abnormalities.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
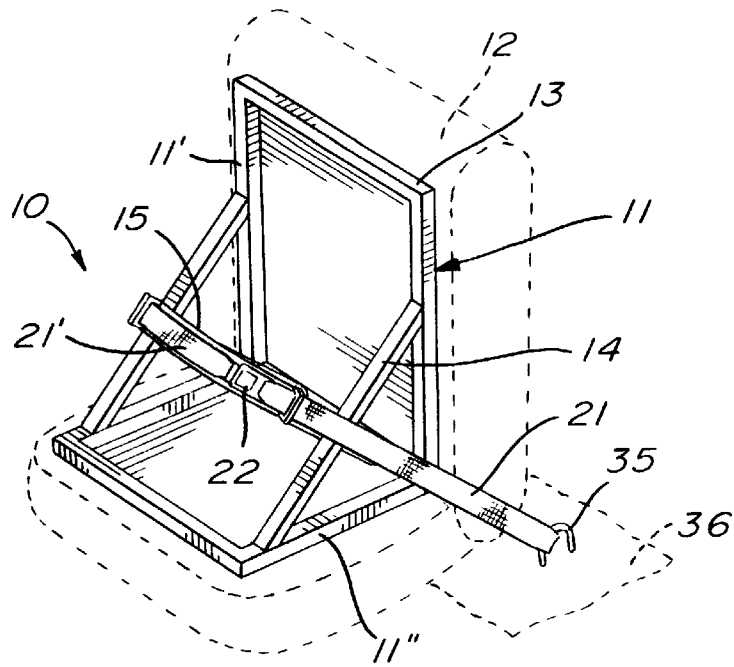
FIG. 1 is a perspective view of the vehicle safety belt test apparatus disposed on a vehicle seat of a vehicle.
Figure 2:
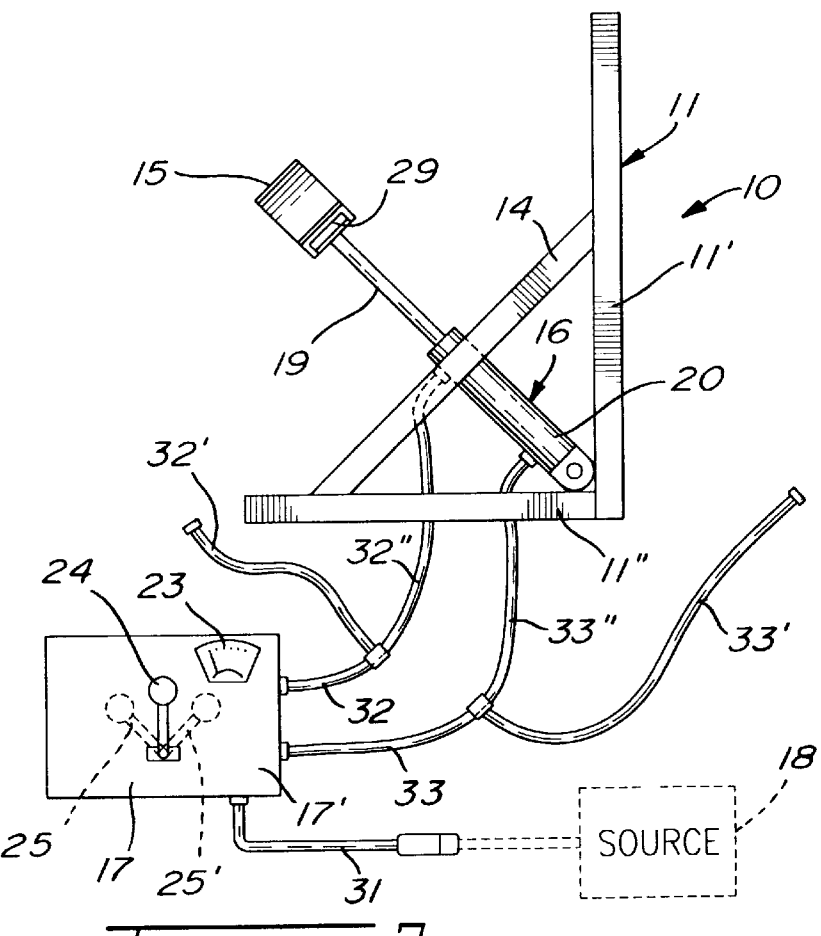
FIG. 2 is a side view of the vehicle safety belt test apparatus.

Referring now to the drawings and more particularly to FIGS. 1 and 2, there is shown generally at 10, the safety belt test apparatus of the present invention. The apparatus comprises a frame 11 which is constructed such as to be positioned on a seat 12 of a vehicle. The frame is formed of interconnected frame members 13 which are disposed to distribute pressure substantially evenly on the seat 12. As shown more clearly in FIG. 2, the frame is an L-shaped frame defining a backrest section 11' and a seat section 11" connected transversely thereto. Bracing frame members 14 solidify the orientation between the backrest section 11' and the seat section 11".

A seat belt support means in the form of a convexly curved member 15 is secured to one or more pistons 16 and extends at an angle between the backrest section 11' and the seat section 11" of the frame. The pistons 16 are connected to a control device 17 which is connected to a pressure source 18 whereby to provide pressurized fluid to the pistons to displace the piston rod 19 of the piston outwardly or inwardly of the piston cylinder 20.

As shown in FIG. 1, a pair of spaced apart seat belt portions 21 and 21' are positioned over the convexly curved support member 15 and secured taut thereover by connecting the buckle portions 22 of the seat belt portions 21, 21'. Once the seat belt portions 21, 21' are secured over the convexly curved support member 15, pressure is then applied to the pistons 16 to extend their piston rods 19 whereby to apply a predetermined force on the seat belt to test the restraining strength of the seat belt. The control device is provided with a pressure gauge 23 to provide a visual display to an operator person to indicate to that person the amount of pressure being applied to the belt. A control lever 24 is provided to direct the pressure to the piston cylinder in a rod extending direction or in a rod retracting direction as illustrated in phantom lines when the lever 24 is at positions 25 and 25', respectively.

Figure 3:
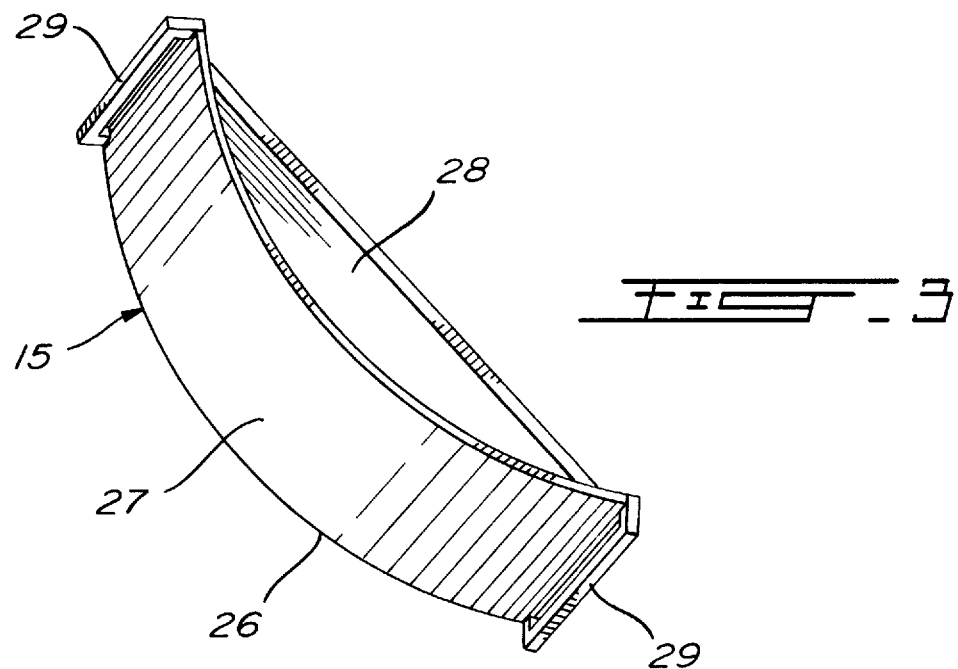
FIG. 3 is a perspective view showing the construction of the convexly curved support member.
Figure 4:
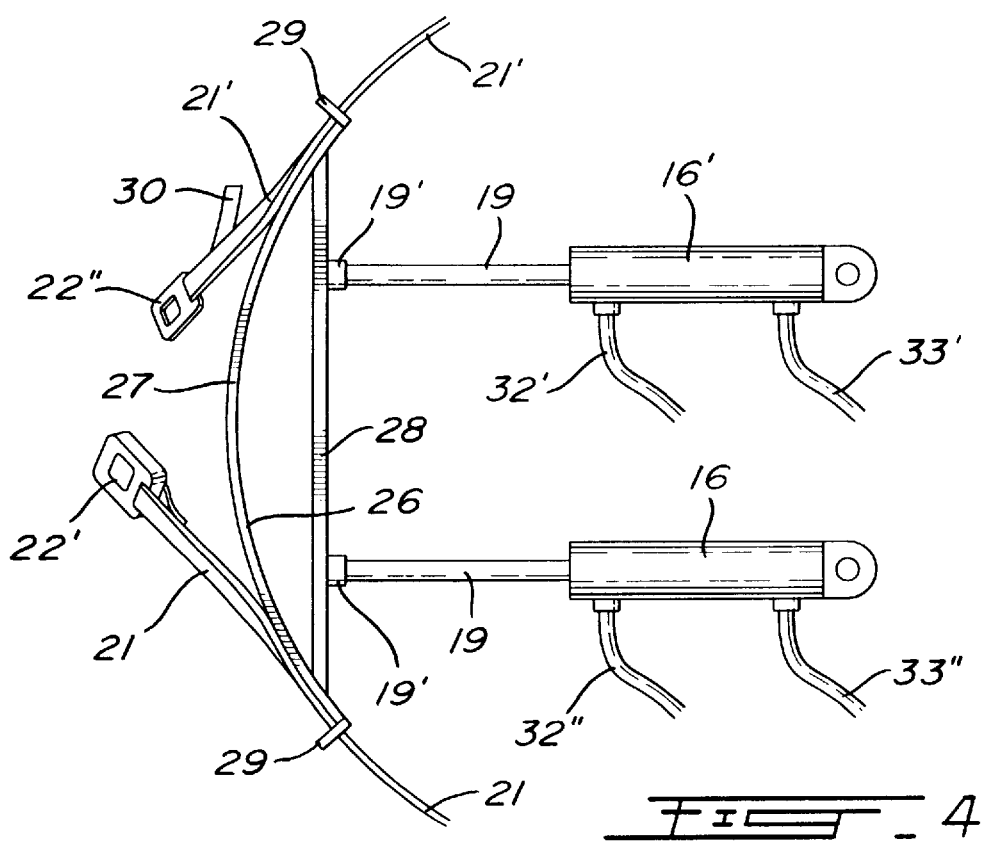
FIG. 4 is a side view of the convexly curved support member showing its securement to a pair of pistons and also showing the manner in which free end sections of spaced-apart seat belt portions are disposed relative thereto.

Referring now to FIG. 3, there is shown the construction of the convexly curved support member 15. As hereinshown it consists of a flat curved metal bar 26 having a top flat surface 27. A brace plate 28 is secured under the metal bar 26 and to which piston rod ends 19' are secured, as shown in FIG. 4. At opposed ends of the flat curved metal bar 26, there is provided belt restraining guide means in the form of inverted U-shaped rods which are welded to the ends of the flat curved metal bar 26 and these constitute rigid guide channels 29. The channels 29 are dimensioned to receive therethrough the buckle portions 22' and 22" which are secured respectively to the belt portions 21 and 21' as illustrated in FIG. 4. As shown in FIG. 4, the male buckle portion 22" is received in the female buckle portion 22' and by pulling the free end 30 of the belt portion 21' the belt is disposed taut and flat over the curved surface 27 of the curved metal bar 26. In order to test the strength of the seat belt the pistons 16 and 16' are actuated, as previously described, to extend their piston rods 19 to displace the support metal bar 26 further away from the frame 11.

Referring again to FIG. 2 it can be shown that the housing 17' of the control device 17 is provided with an inlet pneumatic conduit connector 31 providing connection to a pressure source 18, herein a pneumatic pressure source which one finds available in automobile service garages. The outlet conduits 32 and 33 are provided with branches 32' and 32" which connect respectively to one end of an associated one of the piston cylinders 16 and 16'. The other conduit 33 also has two branches 33' and 33" which also connect respectively to the other end connection of the pair of piston cylinders, as clearly illustrated in FIG. 4.

Briefly summarizing the operation of the test apparatus, the frame 10 is positioned at a desired location on a vehicle seat, such as the vehicle seat 12 as shown in FIG. 1. The pistons 16 are connected to the pneumatic conduits of the control device 17. Opposed free ends of two spaced-apart seat belt portions 21 and 21' are positioned over the belt support metal bar 26 and the buckle 22 is secured with the belt taut over the flat top surface of the support bar 26. The pistons are then actuated by moving the lever 24 to its position 25 as shown in FIG. 2 whereby to extend the piston rod 19 from the piston cylinders 20 until a predetermined force, as indicated on the pressure gauge 23, is attained. This force can be maintained for a short amount of time and thereafter the pressure is released. The seat belts, the buckles and their attachment 35, as shown in FIG. 1, are verified to determine if there is any damage to the belts, the buckles or any fissures or weaknesses at the floor attachment.

It is within the ambit of the present invention to cover any obvious modifications of the preferred embodiment described herein, provided such modifications fall within the scope of the appended claims.

I claim:

1. A vehicle safety belt test apparatus comprising a frame adapted to be positioned on a seat of a vehicle and having interconnected frame members disposed to distribute pressure substantially evenly on said seat, piston means secured to said frame, seat belt support means secured to said piston and adapted to receive opposed free ends of two spaced-apart seat belt portions of a seat belt thereover with a buckle of said seat belt securing said opposed free ends together over said belt support means, said seat belt portions being secured at a securing end to a vehicle frame attachment, and control means to actuate said piston means to displace said seat belt support means relative to said frame to exert a predetermined force on said seat belt portions to test the restraining strength of said seat belt and said attachment.

2. A test apparatus as claimed in claim 1 wherein said seat belt support means is further provided with belt restraining guide means to restrain each said seat belt portion in a guided manner over said support means.

3. A test apparatus as claimed in claim 2 wherein said support means is a substantially convexly curved member having a top flat support surface over which said belt portions are disposed.

4. A test apparatus as claimed in claim 3 wherein said belt restraining guide means is comprised by a rigid channel member secured to opposed ends of said convexly curved member and over said top flat support surface and dimensioned to receive therethrough a buckle portion secured to said seat belt portions.

5. A test apparatus as claimed in claim 3 wherein said convexly curved member is constructed from a flat curved metal bar, and a brace secured under said metal bar, said piston means being secured between said brace and said frame.

6. A test apparatus as claimed in claim 5 wherein said piston means is constituted by a pair of pistons each having a piston cylinder and a piston rod, said piston cylinders being secured to said frame, said piston rods each having a piston rod end secured to said brace of said convexly curved member.

7. A test apparatus as claimed in claim 2 wherein said frame is an L-shaped frame defining a backrest section and a seat section formed by said frame members, and bracing frame members interconnecting said backrest and seat sections.

8. A test apparatus as claimed in claim 2 wherein said control means is a fluid pressure control means secured to a fluid pressure source and said piston means, a control switch on said pressure control means to control the pressure applied to said piston means, and indicator means to indicate the amount of pressure fed to said piston means.

9. A test apparatus as claimed in claim 8 wherein said piston means is comprised of a pair of pistons, each piston having a piston cylinder and a piston rod, said piston rods being secured at a piston rod end thereof to said seat belt support means, each said piston cylinders having a pair of fluid pressure conducting pneumatic conduits connected to a housing of said fluid pressure control means, said control switch controlling the direction of fluid pressure through said piston cylinders whereby to extend or retract said piston rods within their respective cylinders to apply a predetermined force on said seat belt and to retract said force or part thereof.

10. A method of testing the strength of a seat belt comprising the steps of:
i) positioning a force distributing support frame at a desired location on a vehicle seat,
ii) positioning opposed free ends of two spaced-apart seat belt portions over a seat belt support means, said seat belt support means being secured to piston means secured to said support frame,
iii) securing buckle portions attached to said belt portions together with said belt portions taut over said support means,
iv) actuating said piston means by control means whereby to apply a predetermined force on said seat belt,
v) removing at least part of said predetermined force, and
vi) inspecting said seat belt and attachments of said seat belt to detect any abnormalities.

11. A method as claimed in claim 10 wherein said step (ii) comprises positioning said opposed free ends of said two spaced-apart seat belt portions through respective belt restraining guide means, and disposing said opposed free ends of said belt portions flat over a flat support surface of said seat belt support means.

* * * * *